United States Patent [19]
Barron

[11] Patent Number: 5,083,930
[45] Date of Patent: Jan. 28, 1992

[54] GROUND ADAPTER

[76] Inventor: Earl L. Barron, P.O. Box 10356, Houston, Tex. 77206

[21] Appl. No.: 240,959

[22] Filed: Sep. 6, 1988

Related U.S. Application Data

[63] Continuation of Ser. No. 49,670, May 13, 1987, Pat. No. 4,768,963, which is a continuation-in-part of Ser. No. 513,319, Jul. 13, 1983.

[51] Int. Cl.[5] .................................................. H01R 4/66
[52] U.S. Cl. ....................................... 439/101; 439/814
[58] Field of Search ................. 439/92, 95, 101, 727, 439/797, 798, 801, 544, 546, 551, 562, 571, 572, 810, 811, 814

[56] References Cited

U.S. PATENT DOCUMENTS

| | | | |
|---|---|---|---|
| 2,794,099 | 5/1957 | Swain | 200/132 |
| 2,956,259 | 10/1960 | Cornell, Jr. | 339/272 |
| 3,374,456 | 3/1968 | Evans | 339/272 |
| 3,902,780 | 9/1975 | Oola | 339/272 |
| 4,248,490 | 2/1981 | Bachle | 339/14 R |

FOREIGN PATENT DOCUMENTS 239275 9/1925 United Kingdom ............... 339/272

*Primary Examiner*—David L. Pirlot
*Attorney, Agent, or Firm*—Neal J. Mosely

[57] ABSTRACT

A ground adapter is disclosed which comprises an electrically conductive metal body having a threaded cylindrical end portion of a size fitting a threaded opening in the wall of an object to be grounded. The metal body has a transversely extending hole at the end portion opposite the threaded end. A small longitudinally extending threaded hole is provided in the end wall of the metal body and intersects the transverse hole for the ground wire. A screw member is positioned in the threaded hole and movable into and out of the transverse hole for anchoring a ground wire in place. In a second embodiment, the transverse hole may be threaded and the longitudinal hole made smooth to receive a ground wire extending therein. Other embodiments include auxiliary connections for securing a metal bonding ribbon in place as well as a grounding wire. One such embodiment clamps a metal bonding ribbon around a pipe or conduit for grounding. Another such embodiment clamps a metal bonding ribbon and a grounding wire together in the ground adapter.

9 Claims, 4 Drawing Sheets

GROUND ADAPTER

CROSS REFERENCE TO RELATED PATENT APPLICATION

This application is a continuation of U.S. patent application Ser. No. 49,670, filed May 13, 1987, U.S. Pat. No. 4,768,963 which is a continuation-in-part of U.S. patent application Ser. No. 513,319, filed July 13, 1983.

BACKGROUND OF THE INVENTION

1. Field of the Invention

This invention relates to new and useful improvements in ground adapters and more particularly to a ground adapter to be threadedly secured on electrical equipment to connect the same to a ground wire and/or to a metal bonding ribbon.

2. Brief Description of the Prior Art

Evans U.S. Pat. No. 3,374,456 discloses multi-piece multiple terminal connector grounding and other purposes.

Bromberg U.S. Pat. No. 3,492,625 discloses a grounding connector for electrical distribution boxes.

De Smidt U.S. Pat. No. 3,144,293 discloses a dual terminal connector for interconnecting a plurality of cables.

Cornell U.S. Pat. No. 2,956,259 discloses a transformer insulator with a combined electrical connector.

Cornell U.S. Pat. No. 2,951,227 discloses a transformer insulator with an electrical connector having a set screw clamp.

SUMMARY OF THE INVENTION

One of the objects of this invention is to provide a new and improved electrical ground adapter for electrical equipment.

Another object is to provide a metallic ground adapter designed for threaded connection to electrical equipment to be grounded and adaptable to secure ground wires of various size.

Another object is to provide a metallic ground adapter designed for threaded connection to electrical equipment to be grounded and adaptable to secure ground wires of various size and a metal bonding ribbon in place.

Still another object is to provide a metallic ground adapter designed for connection to an appliance to be grounded and adaptable to secure ground wires of various size and having means for connecting a metal bonding ribbon to a pipe or conduit for grounding.

Other objects of the invention will become apparent from time to time throughout the specification and claims as hereinafter related.

The above noted objects, and other objects of the invention are accomplished by a ground adapter which comprises a ground adapter with an electrically conductive metal body having a threaded cylindrical end portion of a size fitting a threaded opening in the wall of an object to be grounded. The metal body has a transversely extending hole at the end portion opposite the threaded end. A small longitudinally extending threaded hole is provided in the end wall of the metal body and intersects the transverse hole for the ground wire. A screw member is positioned in the threaded hole and movable into and out of the transverse hole for anchoring a ground wire in place. In a second embodiment, the transverse hole may be threaded and the longitudinal hole made smooth to receive an a ground wire extending therein. Other embodiments include auxiliary connections for securing a metal bonding ribbon in place as well as a grounding wire. One such embodiment clamps a metal bonding ribbon around a pipe or conduit for grounding. Another such embodiment clamps a metal bonding ribbon and a grounding wire together in the ground adapter.

DESCRIPTION OF THE PREFERRED EMBODIMENTS

Figure 1:
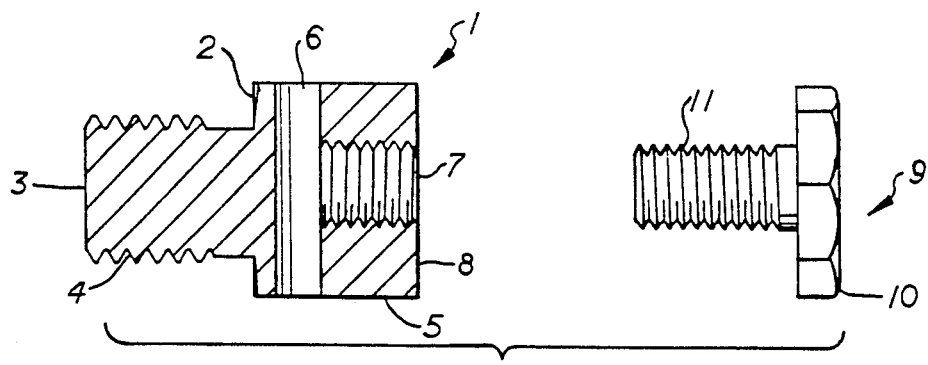
FIG. 1 is an exploded central section of a ground adapter and locking screw illustrating a preferred embodiment of the invention.
Figure 2:
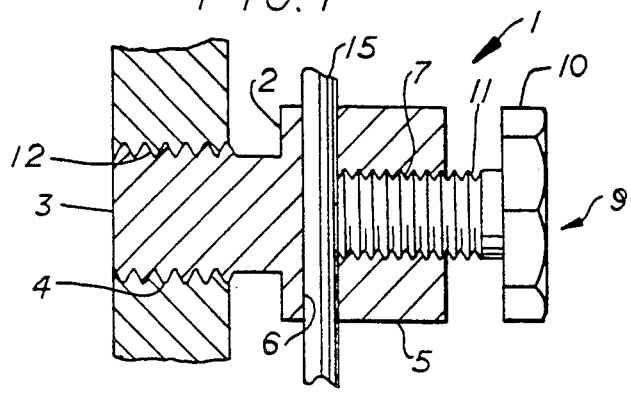
FIG. 2 is a central sectional view of the ground adapter shown in FIG. 1 with the locking screw in place tightening a ground wire therein and secured in the wall of an object needing grounding.
Figure 3:
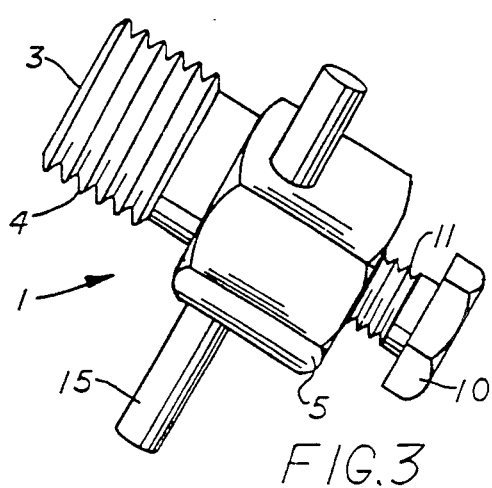
FIG. 3 is a perspective or isometric view of the ground adapter shown in FIGS. 1 and 2, with the ground wire secured therein.

Referring to the drawings by numerals of reference, and more particularly to FIGS. 1-3, there is shown a ground adapter 1 comprising a metal body 2 of electrically conductive metal, preferably Naval brass. Metal body 2 has a smaller end portion 3 of generally cylindrical shape having external threads 4. Metal body 2 has an enlarged end portion 5 which is of hexagonal or other polygonal shape for ease of installation with a wrench. The hexagonal enlarged portion 5 has a transverse hole 6 therethrough for receiving a ground wire.

A longitudinally-extending threaded hole 7 extends through the end face 8 of enlarged hexagonal portion 5 for receiving a threaded screw for tightening a ground wire in the transverse passage 6. The threaded passage 7 intersects passage 6 and permits a tightening screw to be tightened against wire supported therein. A tightening screw 9 is provided for the ground adapter which consists of a polygonal enlarged head portion 10 and a threaded shank portion 11 which is of a size fitting the threaded hole 7 in the enlarged portion 5 of metal body 2.

In FIG. 2, the ground adapter 1 is shown installed in a threaded opening or recess 12 in the metal wall 13 of an apparatus 14 (e.g., a transformer, or the like) requiring electrical grounding. A ground wire 15 is shown inserted in the transverse hole 6 and secured in place by screw 9 being tightened thereagainst. An isometric view of the ground adapter 1 with the wire 15 installed in place is shown in FIG. 3.

Figure 4:
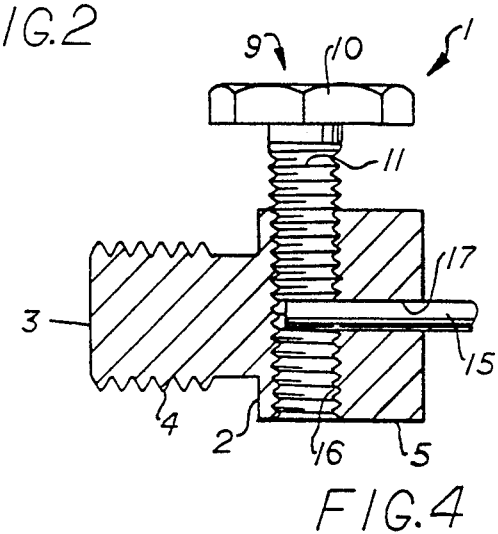
FIG. 4 is a central sectional view of an alternate embodiment of the ground adapter.

In FIG. 4, there is shown an alternate view of ground adapter 1 in which the adapter has been modified by providing a threaded transverse hole 16 in place of the unthreaded hole 6 in the embodiment of FIGS. 1 and 2. In this embodiment, the tightening screw 9 is inserted into the threaded hole 16. In this embodiment, the laterally extending hole 7 is replaced with an unthreaded hole 17 in which wire 15 is positioned. Ground wire 15 is positioned in unthreaded hole 17 and held in place by tightening screw 9 being tightened thereagainst.

OPERATION

The operation of the foregoing embodiments of this invention should be apparent from the above description but will be restated briefly for clarity. The ground adapter 1 is adaptable for a variety of applications. Ground adapter 1 is provided commercially in a number of sizes with the cylindrical portion 3 having threads 4 of a size fitting any threaded opening or threaded recess on the metal object which is to be grounded. The ground adapter 1 is threadedly positioned in a recess or aperture in a metal object to be grounded. The typical sizes for commercial use of this type of ground adapter are ½" and ⅝" diameter threaded portions for fitting standard openings on equipment such as transformers and the like.

The aperture 6 in the embodiment shown in FIGS. 1 and 2 and the apertures 17 in the embodiment of FIG. 4 may handle a variety of sizes of wire for grounding. The commercially used wire sizes for grounding vary from a #6 to a #12 wire. This ground adapter is easily installed and connected to electrical equipment of various types and facilitates the easy installation and connection of ground wires to a neutral ground or to a ground rod or to a support insulator or any other ground device. The ground adapter allows for flexibility in wire size and for variation in size for fitting to the electrical equipment to be grounded.

ANOTHER EMBODIMENT

Figure 5:
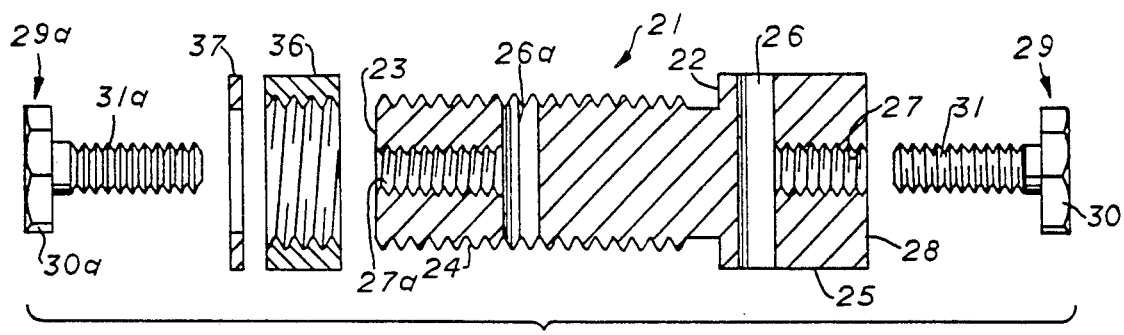
FIG. 5 is an exploded central section of a ground adapter and locking screw illustrating another embodiment of the invention.
Figure 6:
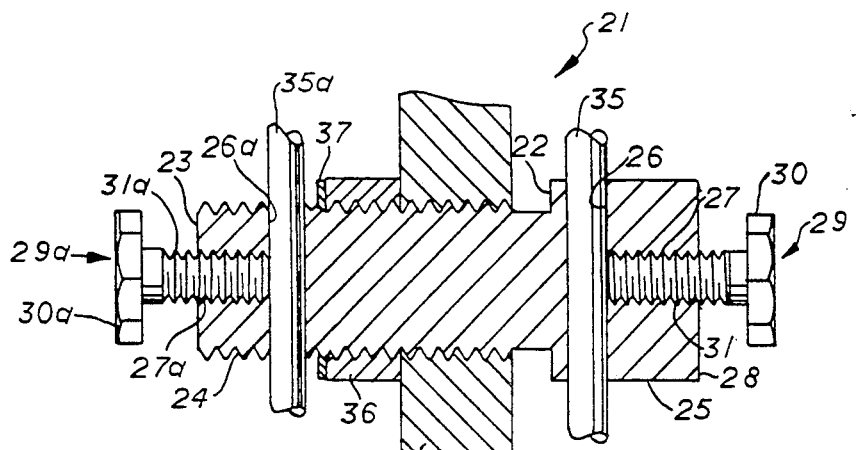
FIG. 6 is a central sectional view of the ground adapter shown in FIG. 5 with the locking screw in place tightening a ground wire therein and a second locking screw tightening a ground wire in side the case on which the ground adapter is mounted and further showing a locking mechanism preventing removal of the ground adapter.
Figure 7:
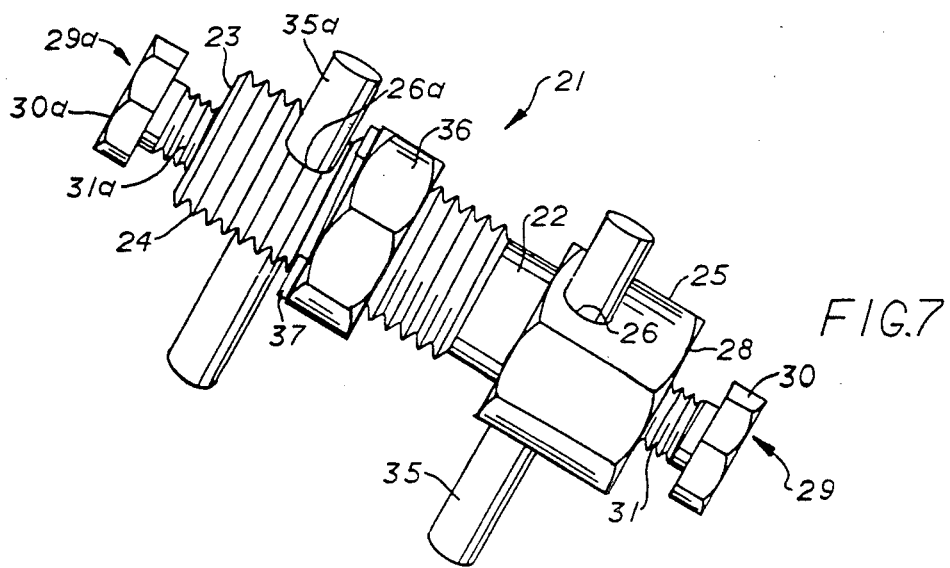
FIG. 7 is an isometric or perspective view of the ground adapter shown in FIG. 6.

In FIGS. 5-7, there is shown a ground adapter 21 comprising a metal body 22 of electrically conductive metal, preferably Naval brass. Metal body 22 has a smaller end portion 23 of generally cylindrical shape having external threads 24. Metal body 22 has an enlarged end portion 25 which is of hexagonal or other polygonals shape for ease of installation with a wrench. The hexagonal enlarged portion 25 has a transverse hole 26 therethrough for receiving a ground wire.

A longitudinally-extending threaded hole 27 extends through the end face 28 of enlarged hexagonal portion 25 for receiving a threaded screw 29 for tightening a ground wire 35 in the transverse passage 26. The threaded passage 27 intersects passage 26 and permits a tightening screw to be tightened against wire supported therein. A tightening screw 29 is provided for the ground adapter which consists of a polygonal enlarged head portion 30 and a threaded shank portion 31 which is of a size fitting the threaded hole 27 in the enlarged portion 25 of metal body 22.

A longitudinally-extending threaded hole 27a extends through the end face of threaded portion 23 for receiving a threaded screw 29a for tightening a ground wire 35 in a transverse passage 26a in the threaded portion 23. The threaded passage 27a intersects passage 26a and permits a tightening screw 29a to be tightened against wire 35a supported therein. A tightening screw 29a is provided for the ground adapter which consists of a polygonal enlarged head portion 30a and a threaded shank portion 31a which is of a size fitting the threaded hole 27a in the threaded 23 of metal body 22. A nut 36 is provided to secure the ground adapter on wall 33 and prevent its removal therefrom. A retaining ring 37 prevents removal of the ground adapter from outside the supporting wall.

In FIG. 6, the ground adapter 21 is shown installed in a threaded opening or recess 32 in the metal wall 33 of an apparatus 34 (e.g., a transformer, or the like) requiring electrical grounding. Ground wires 35 and 35a are shown inserted in the transverse holes 26 and 261 and secured in place by screws 29 and 29a being tightened thereagainst. An isometric view of the ground adapter 21 with the wires 35 and 35a installed in place is shown in FIG. 7.

OPERATION

The operation of the foregoing embodiments of this invention should be apparent from the above description but will be restated briefly for clarity. The ground adapter 21 is adaptable for a variety of applications. Ground adapter 21 is provided commercially in a number of sizes with the cylindrical portion 23 having threads 24 of a size fitting any threaded opening or threaded recess on the metal object which is to be grounded. The ground adapter 21 is threadedly positioned in a recess or aperture in a metal object to be grounded. The typical sizes for commercial use of this type of ground adapter are ½" and ⅝" diameter threaded portions for fitting standard openings on equipment such as transformers and the like.

The apertures 26 and 26a in the embodiment shown in FIGS. 5 and 6 may handle a variety of sizes of wire for grounding. The commercially used wire sizes for grounding vary from a #6 to a #12 wire. This ground adapter is easily installed and connected to electrical equipment of various types and facilitates the easy installation and connection of ground wires to a neutral ground or to a ground rod or to a support insulator or any other ground device. The ground adapter allows for flexibility in wire size and for variation in size for fitting to the electrical equipment to be grounded. As described above, ground wires may be installed both outside and inside the case on which the ground adapter is mounted and the retaining ring 37 and nut 36 prevent removal of the ground adapter from outside the case.

ANOTHER EMBODIMENT

In FIGS. 8-11, there is shown another embodiment of a ground adapter 41 comprising a metal body 42 of electrically conductive metal, preferably Naval brass. Metal body 42 has a smaller end portion 43 of generally cylindrical shape having external threads 44. Metal body 42 has an enlarged end portion 45 which is of hexagonal or other polygonal shape for ease of installation with a wrench. The hexagonal enlarged portion 45 has a transverse hole 46 for receiving a ground wire 55 and a slot 56 for receiving a metal bonding ribbon 57.

A longitudinally-extending threaded hole 47 extends through the end face 48 of enlarged hexagonal portion 45 for receiving a threaded screw for tightening a ground wire in the transverse passage 46. The threaded passage 47 intersects passage 46 and slot 57 and permits a tightening screw to be tightened against wire and metal bonding ribbon supported therein. A tightening screw 49 in the ground adapter has a polygonal enlarged head portion 50 and a threaded shank portion 51 which is of a size fitting the threaded hole 47 in the enlarged portion 45 of metal body 42.

Figure 11:
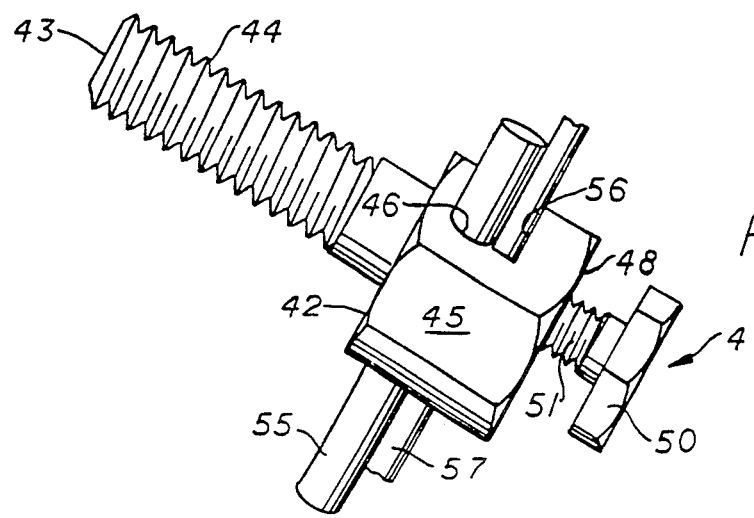
FIG. 11 is a perspective or isometric view of the ground adapter shown in FIG. 8 and 9, with the ground wire and bonding ribbon secured therein.

Ground adapter 41 may be installed in a threaded opening or recess in a metal wall of an apparatus (e.g., a transformer, or the like) requiring electrical grounding, as described for the other embodiments. A ground wire 55 is shown inserted in the transverse hole 46 and a metal bonding ribbon 57 is inserted in slot 56 and secured in place by screw 49 being tightened thereagainst. An isometric view of ground adapter 41 with the wire 55 and metal bonding ribbon 57 installed in place is shown in FIG. 11. This ground adapter is especially useful in connection with the fiber optics splicing case such as the Western Electric UBIC case.

OPERATION

The operation of the foregoing embodiment should be apparent from the above description but will be restated briefly for clarity. Ground adapter 41 is adaptable for a variety of applications. Ground adapter 41 is provided commercially in a number of sizes with the cylindrical portion 43 having threads 44 of a size fitting any threaded opening or threaded recess on the metal object which is to be grounded. Ground adapter 41 is threaded into a recess or aperture in a metal object to be grounded. The typical sizes for commercial use of this type of ground adapter are ½" and ⅜" diameter threaded portions for fitting standard openings on equipment such as transformers and the like.

Figure 8:
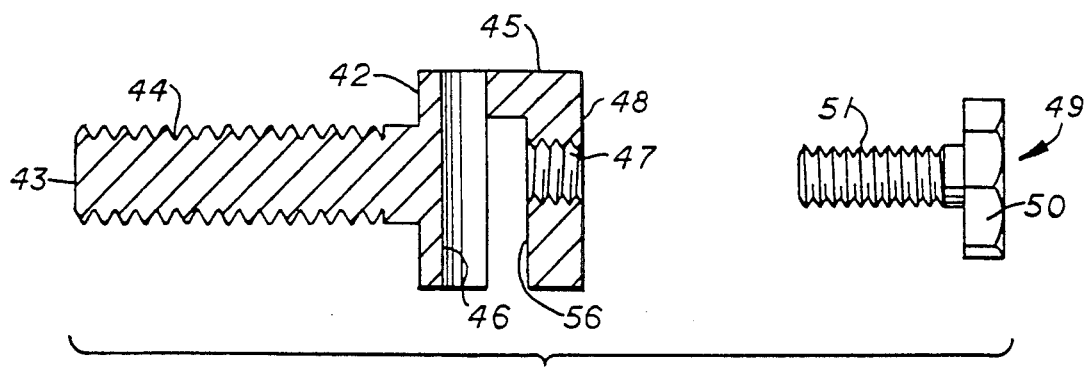
FIG. 8 is an exploded central section of a ground adapter and locking screw illustrating still another embodiment of the invention.
Figure 9:
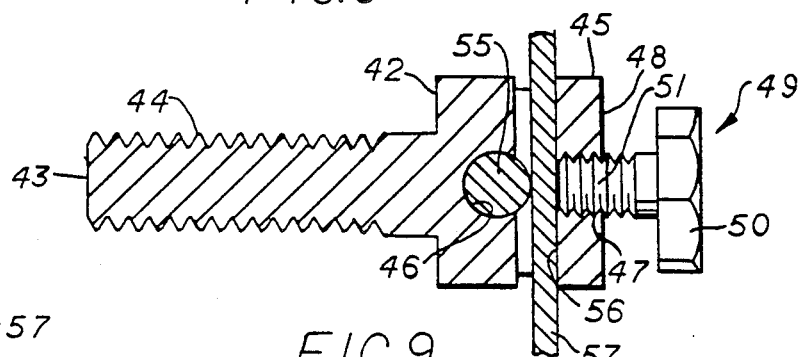
FIG. 9 is a central sectional view of the ground adapter shown in FIG. 8 with the locking screw in place tightening a ground wire and bonding ribbon therein.
Figure 10:
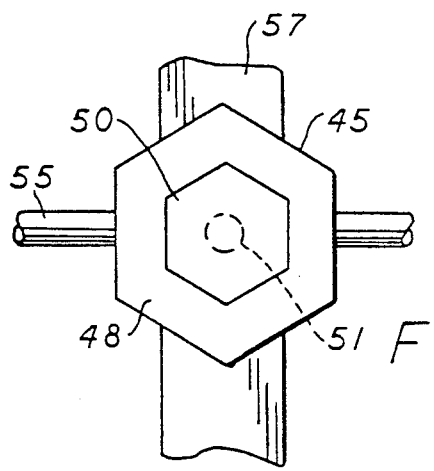
FIG. 10 is an end view of the ground adapter of FIG. 9.

The aperture 46 in the embodiment shown in FIGS. 8 and 9 may handle a variety of sizes of wire for grounding. The commercially used wire sizes for grounding vary from a #6 to a #12 wire. This ground adapter is easily installed and connected to electrical equipment of various types and facilitates the easy installation and connection of ground wires to a neutral ground or to a ground rod or to a support insulator or any other ground device. The ground adapter allows for flexibility in wire size and for variation in size for fitting to the electrical equipment to be grounded. The ground adapted shown is one in which the ground wire and metal bonding ribbon are both secured by the same securing screw 49.

ANOTHER EMBODIMENT

Figure 12:
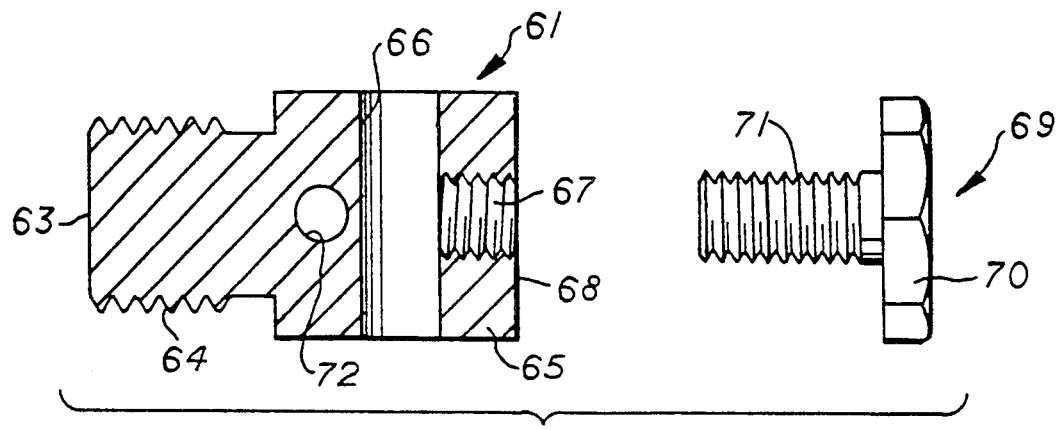
FIG. 12 is a central sectional view of an alternate embodiment of the ground adapter having a configuration for clamping two different wires.
Figure 13:
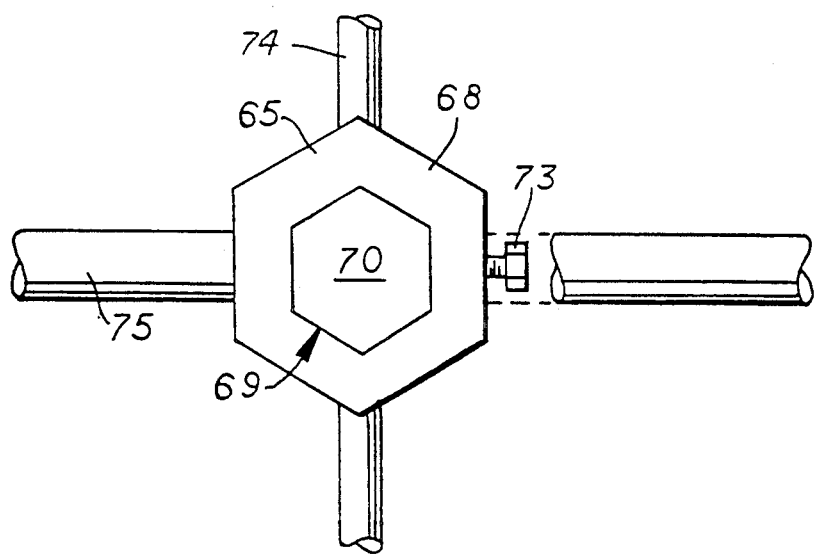
FIG. 13 is an end view of the ground adapter of FIG. 12 showing the clamping screw for the second grounding wire.

In FIGS. 12-13, there is shown still another embodiment of a ground adapter 61 comprising a metal body 62 of electrically conductive metal, preferably Naval brass. Metal body 62 has a smaller end portion 63 of generally cylindrical shape having external threads 64. Metal body 62 has an enlarged end portion 65 which is of hexagonal or other polygonal shape for ease of installation with a wrench. The hexagonal enlarged portion 65 has a first transverse hole 66 for receiving a ground wire 75 and a second transverse hole 72 for receiving another wire 74.

A longitudinally-extending threaded hole 67 extends through the end face 68 of enlarged hexagonal portion 65 for receiving a threaded screw for tightening a ground wire in the transverse passage 66. The threaded passage 67 intersects passage 66 and permits a tightening screw to be tightened against wire 75 supported therein.

A tightening screw 69 in the ground adapter has a polygonal enlarged head portion 70 and a threaded shank portion 71 which is of a size fitting the threaded hole 67 in the enlarged portion 65 of metal body 62. A tightening screw 73 is threaded in a hole intersecting the second transverse hole 72 to clamp a wire 74 in place. Ground adapter 61 may be installed in a threaded opening or recess in a metal wall of an apparatus (e.g., a transformer, or the like) requiring electrical grounding, as described for the other embodiments.

While this invention has been described fully and completely with special emphasis on several preferred embodiments, it should be understood that, within the scope of the appended claims, the invention may be practiced otherwise than as specifically described.

I claim:

1. The combination with a metal wall of an object requiring electrical grounding and having a threaded opening or recess therein, and an electrical ground, of an electrical ground adapter connected to said electrical ground, comprising a one-piece body of electrically conductive metal having a cylindrical portion externally threaded at one end and having an enlarged end portion at the other end of polygonal shape integral therewith and having an outer end face, said threaded cylindrical portion being of a size fitting said threaded opening or recess, said enlarged head portion having a transverse passage therethrough and a longitudinal extending passage from the outer end face of said enlarged end portion to intersect said transverse passage, said passages having cylindrical walls and the wall of at least one of said passages being internally threaded, a single clamping screw threadedly fitted in said one threaded passage and having an enlarged portion for manual operation and an end movable into said intersecting passage, said screw being operable on rotation to have its end moved into or out of said intersecting passage, and a ground wire connected to said electrical ground positioned in the other of said passages and secured in place by said single clamping screw by movement of its end into the other passage clamping said wire against the wall thereof.

2. A combined structure according to claim 1 in which said longitudinally extending passage is threaded.

3. A combined structure according to claim 1 in which said transverse passage is threaded.

4. An electrical round adapter, for connection to an electrical ground, for use with a metal wall of an object requiring electrical grounding and having a threaded opening therein, said electrical ground adapter comprising a one-piece body of electrically conductive metal having a cylindrical portion externally threaded at one end and having an enlarged end portion at the other end of polygonal shape integral therewith and having an outer end face, said threaded cylindrical portion being of a size fitting said threaded opening.

said enlarged end portion having a transverse passage therethrough and a longitudinally extending passage from the outer end face of said enlarged end portion to intersect said transverse passage, said passages having cylindrical walls and the wall of at least one of said passages being internally threaded, a clamping screw threadedly fitted in said one threaded passage and having an enlarged portion for manual operation and an end movable into said intersecting passage, said screw being operable on rotation to have its end moved into or out of said intersecting passage, said other passage being adapted to receive a wire connected to an electrical ground to be secured in place by said clamping screw by movement of its end into the other passage clamping said wire against the wall thereof.

5. An electrical ground adapter according to claim 4 in which said body and clamping screw are of brass.

6. An electrical ground adapter according to claim 4 additionally including a second transverse passage in said body in a plane separated from said first named transverse passage and extending at an angle thereto, a threaded passage intersecting said second transverse passage, and a clamping screw threadedly fitted in said last named threaded passage and having an enlarged portion for manual operation for clamping a wire in said second transverse passage.

7. A method of electrical grounding, which comprises providing an object requiring electrical grounding having a metal wall with a threaded opening or recess therein, providing an electrical ground for said object, providing an electrical ground adapter comprising a one-piece body of electrically conductive metal having a cylindrical portion externally threaded at one end and having an enlarged end portion at the other end of polygonal shape integral therewith and having an outer end face, said threaded cylindrical portion being of a size fitting said threaded opening or recess, said enlarged head portion having a transverse passage therethrough and a longitudinal extending passage from the outer end face of said enlarged end portion to intersect said transverse passage, said passages having cylindrical walls and the wall of at least one of said passages being internally threaded, a single clamping screw threadedly fitted in said one threaded passage and having an enlarged portion for manual operation and an end movable into said intersecting passage, said screw being operable on rotation to have its end moved into or out of sad intersecting passage, securing said ground adapter on or in said threaded opening or recess, inserting one end of a ground wire in said intersecting passage and securing the same in place by said tightening said single clamping screw to move its end into said intersecting passage clamping said wire against the wall thereof, and connecting the other end of said ground wire to said electrical ground.

8. A method according to claim 7 in which said ground adapter body longitudinally extending passage is threaded and said intersecting passage is unthreaded.

9. A method according to claim 7 in which said ground adapter body transverse passage is threaded and said intersecting passage is unthreaded.

* * * * *